US009696326B2

(12) United States Patent
Parmee

(10) Patent No.: US 9,696,326 B2
(45) Date of Patent: Jul. 4, 2017

(54) TEST APPARATUS

(71) Applicant: CHEYNEY DESIGN & DEVELOPMENT LIMITED, Royston (GB)

(72) Inventor: Richard John Parmee, Royston (GB)

(73) Assignee: CHEYNEY DESIGN & DEVELOPMENT LIMITED, Royston (GB)

( * ) Notice: Subject to any disclaimer, the term of this patent is extended or adjusted under 35 U.S.C. 154(b) by 421 days.

(21) Appl. No.: 14/533,844

(22) Filed: Nov. 5, 2014

(65) Prior Publication Data

US 2015/0052967 A1 Feb. 26, 2015

Related U.S. Application Data

(63) Continuation of application No. 12/922,222, filed as application No. PCT/GB2009/000707 on Mar. 16, 2009, now abandoned.

(30) Foreign Application Priority Data

Mar. 14, 2008 (GB) .................................. 0804764.9

(51) Int. Cl.

| | |
|---|---|
| ***G01N 35/00*** | (2006.01) |
| ***G06Q 10/00*** | (2012.01) |
| ***G06Q 50/04*** | (2012.01) |
| *G01N 1/28* | (2006.01) |

(52) U.S. Cl.

CPC ....... *G01N 35/00623* (2013.01); *G06Q 10/20* (2013.01); *G06Q 50/04* (2013.01); *G01N 2001/2893* (2013.01); *Y02P 90/30* (2015.11)

(58) Field of Classification Search

USPC ....................................................... 73/864.91

See application file for complete search history.

(56) References Cited

U.S. PATENT DOCUMENTS 3,318,402 A * 5/1967 Kendrick ............... G01G 13/00 177/46

3,899,915 A * 8/1975 Williams, Jr. ....... G01G 11/006 177/245

(Continued)

*Primary Examiner* — Paul West

*Assistant Examiner* — Mark A Shabman

(74) *Attorney, Agent, or Firm* — Heslin Rothenberg Farley & Mesiti P.C.; Jeff Rothenberg, Esq.

(57) ABSTRACT

A test sample is provided for testing performance of measuring and monitoring equipment for production lines, for example for foodstuffs or pharmaceuticals, and in particular, contamination monitoring equipment employing X-rays and/or metal detectors to spot foreign bodies in packaged products. The test sample may comprise a laminated card enclosing a standardised test piece such as a metal particle of specified size. The card or other sample may bear at least one identification containing a barcode, readable by an optical scanner. To test the equipment, a card is placed on a product package passing through the equipment, the optical scanner reads the barcode to confirm that the correct test sample has been submitted, and the results for the test sample are recorded in a computer log. If the results do not match those expected from the particular test sample submitted, the equipment fails the test and requires recalibration or repair.

20 Claims, 2 Drawing Sheets

3

1

2

4

(56) References Cited

U.S. PATENT DOCUMENTS

Figure 1:
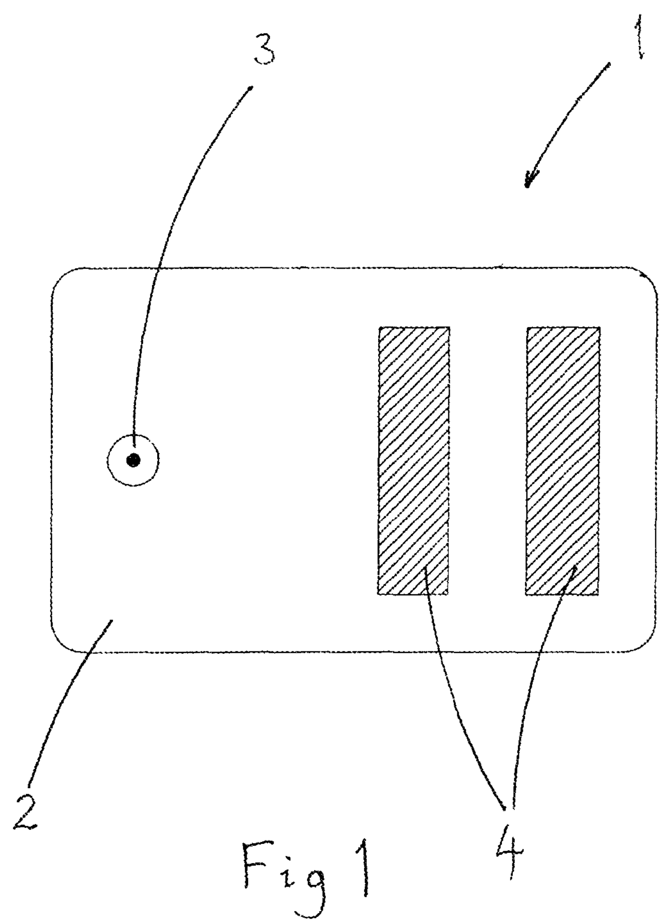

| | | | | | |
|---|---|---|---|---|---|
| 5,148,881 | A * | 9/1992 | Leisinger | G01G 23/012 177/229 |
| 5,257,741 | A * | 11/1993 | Rode | B02C 19/0081 241/100 |
| 5,374,395 | A * | 12/1994 | Robinson | G01N 21/253 422/562 |
| 5,377,697 | A * | 1/1995 | Deutsch | A24C 5/3406 131/330 |
| 5,735,387 | A * | 4/1998 | Polaniec | G01N 35/04 198/465.1 |
| 5,898,169 | A * | 4/1999 | Nordbryhn | G01B 11/2433 250/223 B |
| 6,802,659 | B2 * | 10/2004 | Cremon | B41J 5/30 400/61 |
| 7,178,416 | B2 * | 2/2007 | Whelan | B01L 3/545 73/61.48 |
| 8,001,825 | B2 * | 8/2011 | Pugh | G01N 33/48771 422/403 |
| 2002/0052703 | A1 * | 5/2002 | Tabet | G01G 23/00 702/101 |
| 2004/0046028 | A1 * | 3/2004 | Guntveit | B07C 5/3412 235/462.14 |
| 2004/0265175 | A1 * | 12/2004 | Witty | G01N 21/05 422/68.1 |
| 2006/0169749 | A1 * | 8/2006 | Cooper | B23K 20/10 228/144 |
| 2007/0053793 | A1 * | 3/2007 | Maeda | G01N 35/00594 422/63 |
| 2008/0047760 | A1 * | 2/2008 | Georgitsis | G01G 11/04 177/1 |
| 2011/0048104 | A1 * | 3/2011 | Parmee | G01N 21/274 73/1.79 |

* cited by examiner

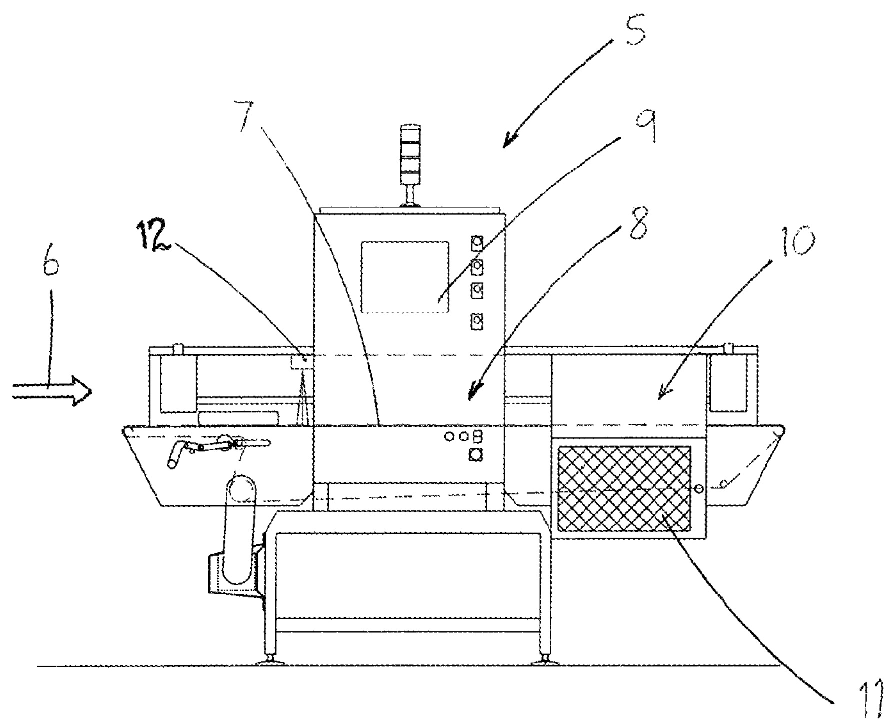
Fig 2A
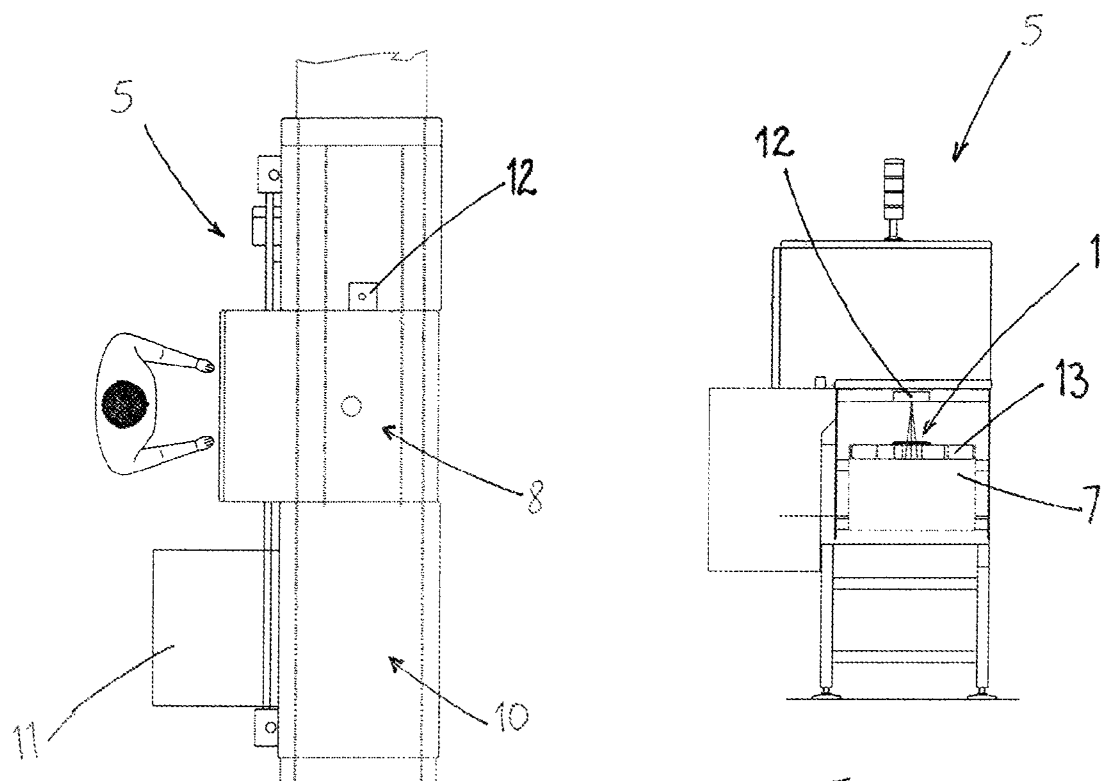
Fig2B
Fig2C

TEST APPARATUS

CROSS REFERENCE TO RELATED APPLICATIONS

This application is a continuation of U.S. patent application Ser. No. 12/922,222 filed on Sep. 13, 2010, which is a national stage filing under Section 371 of International Application No. PCT/GB2009/000707 filed on Mar. 16, 2009, and published in English on Sep. 17, 2009 as WO 2009/112852, and claims priority of GB application number 0804764.9 filed on Mar. 14, 2008, the entire disclosure of all of these applications being hereby incorporated herein by reference.

BACKGROUND ART

The present invention relates to testing and calibration systems for production line monitoring equipment. More particularly, but not exclusively, it relates to an apparatus and method for confirming the correct operation of foreign body monitoring equipment.

It is important to ensure that goods leaving a production line are not contaminated by extraneous material. This is particularly the case when the line is producing goods such as foodstuffs or pharmaceuticals. Monitoring systems are therefore used to scan products on the line. Metal detectors are used to scan for metal particles or the like, while x-ray scanning is capable of detecting objects having only a slightly different radiological density or consistency from the product, such as bones in meat products, glass, mineral stones, and some plastics materials such as poly(vinyl chloride).

It is customary to run test samples through these monitoring systems, initially to ensure that the system has been properly set up, and then either at regular intervals or randomly, in order to confirm the correct operation of the monitoring system. The results of these tests are recorded in a log, for instance as part of a quality assurance system. Customers of food manufacturers will frequently insist on auditing such logs and the associated procedures, as part of their effort to ensure that their own customers are not at risk and have no cause for complaint from contaminated foodstuffs and the like.

The test samples generally comprise laminated test cards or test sticks that can conveniently be placed on or attached to individual products on the production line.

Specifications will often require that the monitoring system on a production line must pick up a test sample of a particular size and type, every time that such a sample is run through the system. If it fails to do so, the monitoring system must be taken out of service and re-calibrated or adjusted. This almost certainly involves shutting down the whole production line, however, which is potentially very expensive. It has become apparent that this situation has in some cases tempted operators to log the use of a specified test sample, but to pass through the system a more easily detectable sample (e.g. a 3 mm metal particle, where the specification is to detect a 1 mm particle). This reduces the frequency of shut-downs for recalibration, but will lead to mis-calibrated monitoring systems potentially passing contaminated goods that they should have detected. It is equally possible that the wrong test sample might be used in error; this would also lead to mis-calibrated systems not being discovered and corrected.

Similar issues are encountered for other monitoring and measuring equipment used on production lines. In each case, the accuracy of measurements is being guaranteed, expressly or by implication, and so it is necessary to test the reliability of the measuring equipment by challenging it regularly with a standard of some form. As above, the prospective cost of taking equipment out of service for readjustment can tempt those responsible for the equipment to submit inappropriate standards to ensure that the test is passed, regardless of the condition of the equipment. Equally, an incorrect standard could be submitted as a simple error.

For example, microwave techniques are used to measure the fat content of food products, and so standard test samples must be run through the respective equipment to confirm that the measured fat contents are meaningful. X-ray techniques are used in the pharmaceutical field to determine the mass of powder delivered to a tabletting die or to a powder inhaler. Calibration discs are used to ensure that these measurements are accurate. In each case, it is important to ensure that the correct standards are used, and ideally that this can be demonstrated to a customer or a regulatory body.

It is hence an object of the present invention to provide apparatus for checking the operation of such measuring and/or monitoring systems, which obviates the above problems and provides a reliable record of a testing regime actually put into effect for the system. It is also an object of the present invention to provide a corresponding method for checking such measuring and/or monitoring systems.

BRIEF SUMMARY OF THE INVENTION

According to a first aspect of the present invention, there is provided a test sample adapted to challenge measuring and/or monitoring equipment of a production line or the like, comprising test standard means of preselected composition, dimensions and/or mass, and machine-readable identification means corresponding to said composition, dimensions and/or mass.

The test standard means may comprise contaminant specimen means adapted to challenge contaminant monitoring equipment.

The contaminant specimen means may comprise material simulating a specific contaminant.

Preferably, said test sample is adapted to be mounted to product means passing along the production line or the like.

Advantageously, said test sample comprises a substantially laminar body disposable on top of said product means.

The test sample may be adapted to be so detachably mountable to the product means as not to cause damage thereto.

Preferably, said identification means is readable by optical sensor means.

Advantageously, said identification means comprises barcode means.

Said barcode means may comprise one-dimensional barcode means.

Alternatively, said barcode means may comprise two-dimensional barcode means.

Said identification means may comprise electronic identification means such as RFID (radio-frequency identification) tag means.

The test standard means may comprise a test standard adapted to challenge equipment for measuring product properties such as weight, size and composition.

According to a second aspect of the present invention, there is provided measuring and/or monitoring equipment for a production line or the like, comprising means to determine a product property, means to report the determination of said property and means adapted to read identification means of a test sample means submitted to the equipment so as to confirm its correct operation.

The measuring and/or monitoring equipment may comprise contamination monitoring equipment, said property being presence or absence of a particular contaminant means.

Said contamination monitoring equipment may comprise X-ray scanning means.

Alternatively or additionally, the contamination monitoring equipment may comprise metal detector means.

Alternatively or additionally, the measuring and/or monitoring equipment may be adapted to measure one or more product properties such as weight, dimensions and/or composition.

Preferably, said test sample means comprises a test sample as described in the first aspect above.

Said reader means preferably comprises optical reader means.

Said reader means advantageously comprises barcode reader means.

The reporting means may comprise alarm means.

The reporting means may comprise log means, such as electronic log file means, optionally remotely accessible, such as via a database server or the like.

Said log means may be adapted to record a sample identity, read from test sample means submitted to the equipment, in association with a product property determination report for said test sample means.

Means may be provided to compare an actual product property determination report for test sample means with a predicted product property determination report therefor.

Said comparison means may base said predicted product property determination report on an identity of the test sample means, as read by the reader means.

The monitoring equipment may be provided with means to alert an operator to submit a test sample means.

Said alerting means may be adapted to inform the operator which test sample means to submit.

According to a third aspect of the present invention, there is provided a method for testing correct operation of measuring and/or monitoring equipment for production line means, comprising the steps of providing test sample means comprising machine-readable identification means, providing measuring and/or monitoring equipment comprising means to read said identification means, submitting said test sample means to said equipment, recording a response of said equipment to the test sample means, reading the identification means of the test sample means to determine an identity thereof, and recording said sample identity in association with said response.

The measuring and/or monitoring equipment may comprise contamination monitoring equipment.

Alternatively or additionally, the measuring and/or monitoring equipment may comprise equipment adapted to measure product properties, such as weight, dimensions and/or composition.

Preferably, said identification means comprises barcode means.

Said identification means preferably comprises data concerning one or more properties of the test sample means, such as composition, dimensions and/or mass.

Said identification means may comprise data concerning a contaminant type, level and/or size that comprises or is simulated by the test sample means.

Said identification means advantageously comprises data concerning a provenance of the test sample means, such as its source, certification data and/or its date of creation and/or certification.

Said identification means may comprise serial number means adapted to enable reference or cross-reference to some or all of said data.

Preferably said recording steps comprise making a record in log means, optionally in electronic log file means.

The method may comprise the steps of providing a schedule for submitting preselected test sample means, and comparing the identification means of the test sample means submitted with that pre-selected in the schedule.

Preferably, the method comprises the step of comparing an actual response for a submitted test sample means to a predicted response therefor.

Advantageously, the method comprises the step of establishing said predicted response based on a sample identity determined by reading the identification means of the submitted test sample means.

The measuring and/or monitoring equipment may comprise measuring and/or monitoring equipment as described in the second aspect above.

The test sample means may comprise a test sample as described in the first aspect above.

BRIEF DESCRIPTION OF THE DRAWING FIGURES

Embodiments of the present invention will now be more particularly described by way of example and with reference to the accompanying drawings, in which FIG. 1 is a plan view of a test sample embodying the present invention; and FIGS. 2A, 2B and 2C are a frontal elevation, a plan view from above and a side elevation respectively of monitoring equipment embodying the present invention.

DETAILED DESCRIPTION

A production line for foodstuffs or pharmaceutical products is provided with a monitoring system to check for the presence of contaminants. For example, a metal detector arrangement may be used to scan for metallic fragments in products. X-ray scanning and imaging or signal integration arrangements may be used to monitor for a range of foreign bodies in the product, as long as they differ in density from the authentic contents of the products in question.

To confirm that such monitoring systems are correctly set-up, and can be relied upon to detect product contamination, test samples are provided which contain standard contaminants (such as metal particles or strips of specified dimensions) or materials simulating standard contaminants. The test samples frequently comprise laminated cards or test sticks within which the standard contaminants, etc, are enclosed. These can conveniently be placed on top of a product passing along the production line, thereby used to challenge the monitoring system, and then removed without having harmed the product.

The monitoring system will typically be programmed with a testing schedule, and will notify an operator when a test sample is due to be passed through the monitoring system as a challenge, and which test sample to use. The monitoring system will also keep a log to confirm that a test sample has been passed through, and whether the monitoring system passed or failed the product bearing the test sample. If the monitoring system passes a test sample that it should have failed, this may lead to the monitoring system (and associated production line) having to be taken out of service until the monitoring system can be re-calibrated.

It is possible in existing monitoring systems for an incorrect test sample to be passed through, whether by accident or deliberately. Thus, if the monitoring system is challenged with a sample that is too easily detected, it may go out of calibration without being noticed, or deliberate or inadvertent maladjustment of system settings may be missed. In either case, contaminated products might as a result be released from the production line and supplied to customers.

Referring now to the Figures, and to FIG. 1 in particular, a test sample 1 embodying the present invention comprises a laminated card 2 with a foreign body test piece 3 enclosed therein. The foreign body test piece 3 is standardised to fit a pre-selected specification criterion; for example, it may comprise a metal particle of specified dimensions.

One or more identification zones 4 are provided on one face of the card 2 (optionally, corresponding zones 4 are provided on both an obverse and a reverse of the card 2 for convenience). Each identification zone 4 carries a barcode (not shown) which encodes data concerning the type of contaminant/foreign body test piece 3 present, its dimensions, a serial number of the test sample 1, and other identifying information such as the origin of the test sample 1, and its date of production and/or issue. Alternatively, some or all of these data may be provided in a database, referenced through the serial number of the test sample 1 encoded into the barcode. The barcode may comprise a one-dimensional code, comprising a series of spaced linear features, or may comprise a two-dimensional array of information, such as those known as "matrix" or "snowflake" codes.

FIGS. 2A to 2C show a piece of monitoring equipment 5 embodying the present invention, suitable for incorporation into a production line. Products pass through the equipment 5 from left to right, as indicated by arrow 6, supported on a moving continuous belt 7. The products are scanned (in this case with an imaging x-ray system) at an inspection point 8, the results being analysed and displayed by a built-in computer 9. If a contaminant is detected, it is logged on an electronic log file and an alarm notifies an operator. At a reject point 10, down-line of the inspection point 8, the particular product in which the contaminant was detected is ejected from the production line into a reject bin 11.

The monitoring equipment 5 of the present invention is provided with a barcode reader 12 located above the moving belt 7, immediately before the inspection point 8. This reader 12 is thus disposed so that it can read a barcode on the identification zone 4 of a test sample 1 placed on top of a product 13 passing along the belt 7 (see FIG. 2C in particular).

The data read from the barcode are then compared to the data for the test sample 1 that was scheduled to be passed through the equipment 5. If the data do not match, the operator is alerted to this fact, so that the correct test sample 1 may be passed through. The electronic log file keeps a record of the test samples 1 actually used, cross-referenced with the outcome of the passage of each test sample 1 through the monitoring equipment 5.

This log file can be audited as desired to provide full confirmation that the specified testing regime has been carried out, in order that customers may rely on products from the line not being contaminated.

In a preferred embodiment, not only is the presence of a contaminant noted and logged, but its signature is also noted and logged. This signature may for example comprise a detected size and/or shape of the contaminant, and/or a detection signal magnitude. Frequently, the signature will result from an algorithm, processing a plurality of independent data items arranged in a multi-dimensional array. The barcode reader 12 reads data from the test sample 1, and from these data an expected signature for that particular test sample 1 is determined, for example by selection from an archive of such signatures. The signature actually detected for the test sample 1 is compared to that expected. If they do not tally within pre-set limits, this is logged and the operator is notified.

This obviates a possible malpractice in which an additional unauthorised contaminant is added (for example, a coin) to ensure that a contaminant is apparently detected when a system is being tested.

The identification of the particular test samples 1 used, their origin and their date allows a full audit trail to be established back to primary standards or to independent certification results. It also allows a check that current standards are in use (the details of specifications might change for example, or some foreign body test pieces 3 might change properties over time and require regular replacement).

The equipment 5 and samples 1 described allow for a much more reliable and foolproof contaminant monitoring regime than existing equipment and samples.

Further embodiments of the present invention are applied to test the correct operation of other measuring equipment used on production lines, for example to check product mass, dimensions or composition.

One example of the use of such equipment is in the preparation of pharmaceutical products, in which it is very important that a tablet, capsule or the like contains a correct dose of an active component. One technique for this is to dispense powdered material into pockets or moulds, conveniently on a disc carrier; the material in each pocket may for example be pressed into a tablet, delivered into a capsule, or loaded into a powder inhaler. X-ray equipment is used to determine the mass of material delivered, and so calibration discs are provided to confirm that the X-ray equipment is measuring accurately. In the present invention, identifying barcodes or the like are applied to the calibration discs, and the X-ray equipment is provided with a scanner to read these. The equipment then determines the mass of the calibration standard, checks that this corresponds (within preselected limits) to the mass expected for the identity read from the barcode and logs these data. An operator is alerted if the mass determined is outside the preselected limits. The log is retained to demonstrate that a reliable calibration and quality control regime is in place.

Another example is the determination of a fat content of a food product (such as meat products, in which the fat content usually specified, or a "low-fat" spread or dessert). The fat content may be determined using microwave apparatus. As above, it is necessary to check the calibration of this apparatus to confirm the reliability of its results. In the present invention, test standards of predetermined fat content are submitted to the apparatus. These standards bear barcodes recording the predetermined fat content and provenance of each test standard. The apparatus is provided with a barcode reader. It reads and logs the identity and provenance of a test standard submitted, the expected fat content that should be determined for the standard, and the fat content actually measured. If the fat content measured differs from the expected fat content by more than permitted limits, an operator is then notified, and the apparatus should be taken out of service for recalibration or other maintenance.

It is believed that other forms of process measurement and/or monitoring would also benefit from the use of test standards that may be automatically identified by the measurement/monitoring apparatus. For example, water contents are often determined by infrared techniques. Packaging seals are often checked by ultrasound techniques, which should be challenged by submitting standard packages with known seal defects. Even conventional check-weighing systems should regularly be challenged with standard weights, to confirm they remain correctly calibrated, within acceptable limits. In all these cases, and many others, it is beneficial to provide a barcode reader, set up to read, from a barcode on a test sample, the identity of the sample and the test results expected from that sample.

While the present invention is described above in terms of barcodes and optical barcode readers, RFID devices may also be useful, particularly where large quantities of sample data are involved. However, in some cases, RFID devices may be less suitable than barcodes, such as where the RFID device might itself appear to be a contaminant, or where the detection technique might damage the RFID device.

It is believed that the approach of adding automatically readable identification means to test samples and standards may be more widely applicable, for example in monitoring apparatus employing vision systems, or in other forms of inspection systems.

The invention claimed is:

1. A test sample adapted to test correct operation of measuring and monitoring equipment of a production line, comprising a contaminant specimen including a contaminant or simulated contaminant and having at least one pre-selected property selected from composition, dimensions and mass, said test sample further comprising machine-readable identification identifying said test sample and corresponding to said pre-selected property of the contaminant specimen, wherein the test sample is co-locatable with a product passing along the production line, such that the test sample and said product pass together through the measuring and monitoring equipment.

2. The test sample as claimed in claim 1, wherein said identification is readable by an optical sensor.

3. The test sample as claimed in claim 1, wherein said identification comprises a barcode.

4. Measuring and monitoring equipment for a production line, comprising contamination monitoring equipment to determine a presence or absence of a preselected contaminant, means to report the determination of the presence or absence of said preselected contaminant, and means adapted to read identification of a test sample comprising a contaminant specimen including a contaminant or simulated contaminant and having at least one pre-selected property selected from composition, dimensions and mass, and comprising machine-readable identification identifying said test sample and corresponding to said pre-selected property of the contaminant specimen, when said test sample is submitted together with a product passing along the production line to the measuring and monitoring equipment so as to confirm correct operation of the measuring and monitoring equipment.

5. The measuring and monitoring equipment as claimed in claim 4, wherein said means adapted to read identification comprises an optical reader.

6. The measuring and monitoring equipment as claimed in claim 5, wherein said means adapted to read identification comprises a barcode reader.

7. The measuring and monitoring equipment as claimed in claim 4, further comprising means to alert an operator when a test sample is due to be passed through the measuring and monitoring equipment.

8. The measuring and monitoring equipment as claimed in claim 7, further comprising means to alert an operator which test sample from a range of available test samples to pass through the measuring and monitoring equipment.

9. The measuring and monitoring equipment as claimed in claim 8, provided with a schedule to define occasions when a test sample is due to be passed through the measuring and monitoring equipment and to define which test sample from the range of available test samples to pass on each said occasion.

10. The measuring and monitoring equipment as claimed in claim 9, adapted to compare an identity of a test sample determined from its machine-readable identification with an identity of the test sample due to be passed through the measuring and monitoring equipment as defined by the schedule.

11. A method for testing correct operation of measuring and monitoring equipment for a production line, said measuring and monitoring equipment comprising contamination monitoring equipment, comprising the steps of: providing a test sample comprising a contaminant specimen including a contaminant or simulated contaminant and having at least one pre-selected property selected from composition, dimensions and mass, said test sample further comprising machine-readable identification identifying said test sample and corresponding to said pre-selected property of the contaminant specimen, providing measuring and monitoring equipment comprising means to read said identification, placing said test sample together with a product passing along the production line, submitting said test sample and said product together to said measuring and monitoring equipment, recording a response of said measuring and monitoring equipment to the test sample, reading the identification of the test sample to determine an identity of the test sample, and recording said identity of the test sample in association with said response.

12. The method as claimed in claim 11, wherein said identification comprises a barcode.

13. The method as claimed in claim 11, wherein said identification comprises data concerning at least one property of the test sample.

14. The method as claimed in claim 11, wherein said identification comprises data concerning at least one of a type, level and size of a contaminant that is represented by the test sample.

15. The method as claimed in claim 11, wherein said identification comprises data concerning a provenance of the test sample.

16. The method as claimed in claim 11, wherein said recording steps comprise making a record in electronic log file.

17. The method as claimed in claim 11, comprising the steps of providing a schedule for submitting pre-selected test samples, and comparing the identification of the test sample submitted with identification of a pre-selected test sample due to be submitted according to the schedule.

18. The method as claimed in claim 17, comprising the further step of alerting an operator and recording when the identification of the test sample submitted does not match the identification of the pre-selected test sample due to be submitted according to the schedule.

19. The method as claimed in claim 11, further comprising the step of comparing an actual equipment response for a submitted test sample to a predicted response based on a sample identity established by reading the identification of the submitted test sample.

20. The method as claimed in claim 19, comprising the further step of alerting an operator and recording when the actual equipment response for a submitted test sample does not match the predicted response based on a sample identity established by reading the identification of the submitted test sample.

* * * * *